(12) United States Patent
Iwata

(10) Patent No.: US 7,556,731 B2
(45) Date of Patent: Jul. 7, 2009

(54) LIQUID CHROMATOGRAPH

(75) Inventor: Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/061,610

(22) Filed: Apr. 2, 2008

(65) Prior Publication Data
US 2008/0245715 A1    Oct. 9, 2008

(30) Foreign Application Priority Data
Apr. 3, 2007    (JP) ............................. 2007-097139

(51) Int. Cl.
*B01D 15/08* (2006.01)
(52) U.S. Cl. .................... 210/198.2; 210/101; 210/656; 210/659
(58) Field of Classification Search ................. 210/656, 210/659, 101, 198.2; 422/70
See application file for complete search history.

(56) References Cited
U.S. PATENT DOCUMENTS

| | | | | |
|---|---|---|---|---|
| 5,117,109 A | * | 5/1992 | Asakawa et al. | 250/288 |
| 5,372,716 A | * | 12/1994 | Levy et al. | 210/198.2 |
| 5,458,783 A | * | 10/1995 | Levy et al. | 210/659 |
| 6,780,325 B1 | * | 8/2004 | Murata et al. | 210/656 |
| 6,802,967 B2 | * | 10/2004 | Masuda et al. | 210/198.2 |
| 6,942,793 B2 | * | 9/2005 | Ito et al. | 210/198.2 |
| 2003/0168392 A1 | * | 9/2003 | Masuda et al. | 210/198.2 |
| 2005/0167348 A1 | | 8/2005 | Iwata | |
| 2005/0218055 A1 | * | 10/2005 | Hayashi et al. | 210/198.2 |

OTHER PUBLICATIONS

Machine Translation of Japan Patent No. 2002-372522, pp. 1-7.*

* cited by examiner

*Primary Examiner*—Ernest G Therkorn
(74) *Attorney, Agent, or Firm*—Cheng Law Group PLLC

(57) ABSTRACT

A liquid chromatograph having a flow passage switching mechanism for switching among a normal analysis flow passage formed by connecting a mobile-phase-sending-unit, a second mixer having a large capacity, a sample injection portion, an analysis column and a detector in this order, a concentration flow passage formed by connecting a concentration liquid sending unit for sending a liquid for transferring a sample to be concentrated, the second mixer, the sample injection portion and a trapping column in this order, and a concentration analysis flow passage formed by connecting the mobile-phase-sending-unit, a first mixer having a smaller capacity than the second mixer, the trapping column, the analysis column and the detector in this order so that any one of the three flow passages is selectively formed, The mobile-phase-sending-unit is set so that the flow rate of a mobile phase becomes smaller when the concentration analysis flow passage is selected than when the normal analysis flow passage is selected.

4 Claims, 2 Drawing Sheets

LIQUID CHROMATOGRAPH

BACKGROUND OF THE INVENTION

1. Field of the Invention

The present invention relates to a liquid chromatograph having a mobile phase flow passage for sending a mobile phase obtained by mixing a plurality of kinds of solvents with a mixer and used for introducing a sample injected from a sample injection portion into an analysis column. Particularly, the present invention relates to a liquid chromatograph having a trapping column for concentrating a dilute sample and allowing the sample to be analyzed in a concentrated state.

2. Description of the Related Art

Generally, in the case of analysis using a high-performance liquid chromatograph, a sample is injected into an analysis flow passage from a sample injection portion, and then transferred into an analysis column by a mobile phase sent by a liquid sending pump, and then separated into individual components by the analysis column. At this time, when the amount of the sample injected from the sample injection portion is large, a sample band in the analysis column is broadened by the action of a solvent contained in the sample, thereby reducing separation performance and making it impossible to achieve highly-sensitive analysis. For this reason, it is not preferred that a large amount of sample solution is injected from the sample injection portion.

However, in the case of analysis of a dilute sample, it is necessary to increase the absolute mass of the sample to achieve sufficient sensitivity, and therefore there is a case where a large amount of sample must be injected from the sample injection portion. In such a case, analysis involving online concentration using a trapping column is often carried out.

In the case of analysis involving online concentration, a sample injected from the sample injection portion is concentrated by trapping it in the trapping column, and then the concentrated sample trapped in the trapping column is separated by an analysis column and analyzed. In this case, in order to examine the concentration efficiency of the trapping column and the degree of deterioration of the analysis column, the same sample is also subjected to normal analysis (i.e., direct analysis) not involving online concentration, and then the results of both analyses are compared to determine a recovery rate. In order to carry out direct analysis to determine the recovery rate, it is necessary to change the flow passage configuration of a liquid chromatograph from a flow passage configuration for online concentration to a flow passage configuration for direct analysis. Such a change in flow passage configuration is very complicated and takes much time, and in addition, attention needs to be paid so that leakage of a mobile phase and a dead volume in a flow passage will not occur even after changing a flow passage configuration. In order to solve such a problem, the present inventor has proposed a liquid chromatograph having flow passage switching valves (see US 2005/0167348 A1). In the liquid chromatograph, a flow passage configuration can be switched between a flow passage configuration for online concentration and a flow passage configuration for direct analysis only by operating the flow passage switching valves.

Meanwhile, liquid chromatographic analysis is carried out using a mobile phase obtained by mixing two or more kinds of solvents, and the mixing ratio between/among the solvents is changed with time. Therefore, in order to promote the mixing of the solvents, a mixer is provided in a flow passage. In such liquid chromatographic analysis, in some cases, a mobile phase is preferably sent at a conventional flow rate of about 50 µL/min to 1 mL/min, and in other cases, a mobile phase is preferably sent at a micro flow rate of 50 µL/min or less.

For example, in the case of direct analysis, a mobile phase is generally sent at a conventional flow rate, but in the case of concentration analysis after sample concentration, a mobile phase is generally sent at a micro flow rate. In a case where a mobile phase is sent at a conventional flow rate, mixing of the mobile phase is preferably promoted using a mixer having a relatively large capacity of about 1 mL. On the other hand, in a case where a mobile phase is sent at a micro flow rate, mixing of the mobile phase is preferably promoted using a mixer having a relatively small capacity of about 5 µL. This is because, in a case where a mixer having a capacity of 1 mL is used when a mobile phase is sent at a flow rate of 5 µL/min, the capacity of the mixer is too large for the flow rate of the mobile phase and therefore a delay as long as about 200 minutes occurs. On the other hand, in a case where a mixer having a capacity of 5 µL is used when a mobile phase is sent at a flow rate of 1 mL/min, the mobile phase cannot be sufficiently mixed. For this reason, in a case where it is necessary to send a mobile phase at various flow rates in a wide range from a micro flow rate to a conventional flow rate in a single system of a liquid chromatograph, the selection of the capacity of a mixer to be used becomes a problem.

SUMMARY OF THE INVENTION

It is an object of the present invention to provide a liquid chromatograph which uses a mixture of a plurality of kinds of solvents as a mobile phase and which enables analysis to be carried out without causing a problem even when the mobile phase is sent at any flow rate within a wide range.

The present invention is directed to a liquid chromatograph including: a mobile-phase-sending-unit having a plurality of solvent flow passages for sending solvents different from each other; a mixer unit provided downstream of the mobile-phase-sending-unit to mix solvents sent from the mobile-phase-sending-unit, the mixer unit having a first mixer and a second mixer having a capacity larger than that of the first mixer; a sample injection portion for injecting a sample; a concentration liquid sending unit for sending a liquid for transferring a sample to be concentrated; a trapping column for concentrating the sample by trapping components of the sample; an analysis column for separating the sample into individual components; a detector for detecting each of the components separated by the analysis column; and a flow passage switching mechanism. The flow passage switching mechanism has a first multi-port valve connected to the second mixer and the sample injection portion, a second multi-port valve connected to the trapping column and the analysis column, and a flow passage for connecting the first multi-port valve and the second multi-port valve to each other. The first mixer is connected to the first multi-port valve, the second multi-port valve or the port-to-port connection flow passage.

The flow passage switching mechanism is used to switch among a normal analysis flow passage formed by connecting the mobile-phase-sending-unit, the second mixer, the sample injection portion, the analysis column and the detector in this order, a concentration flow passage formed by connecting the concentration liquid sending unit, the second mixer, the sample injection portion and the trapping column in this order, and a concentration analysis flow passage formed by connecting the mobile-phase-sending-unit, the first mixer, the trapping column, the analysis column and the detector in this order so that any one of the three flow passages is selectively formed. The mobile-phase-sending-unit is set so that the flow rate of a mobile phase becomes smaller when the concentration analysis flow passage is selected than when the normal analysis flow passage is selected.

In a case where the first mixer is connected to the first multi-port valve, the normal analysis flow passage is formed by connecting the mobile-phase-sending-unit, the first mixer, the second mixer, the sample injection portion, the analysis column and the detector in this order.

In a case where the first mixer is connected to the port-to-port connection flow passage, the normal analysis flow passage is formed by connecting the mobile-phase-sending-unit, the second mixer, the sample injection portion, the first mixer, the analysis column and the detector in this order.

In a case where the first mixer is connected to the second multi-port valve, the first mixer is connected to a port sending a liquid to the trapping column, and the normal analysis flow passage is formed by connecting the mobile-phase-sending-unit, the second mixer, the sample injection portion, the analysis column and the detector in this order.

In the liquid chromatograph according to the present invention, the first mixer is used for promoting the mixing of solvents in the case of concentration analysis, and the second mixer is used for promoting the mixing of solvents in the case of normal analysis. Generally, in the case of normal analysis, a mobile phase is sent at a conventional flow rate larger than 50 μL/min. On the other hand, in the case of concentration analysis, a mobile phase is preferably sent at a micro flow rate of 50 μL/min or less. That is, the second mixer to be used in the case of normal analysis has a capacity suitable for mixing a solvent sent at a conventional flow rate larger than 50 μL/min e.g., about 1 mL. On the other hand, the first mixer to be used in the case of concentration analysis has a capacity suitable for mixing a solvent sent at a micro flow rate of 50 μL/min or less e.g., about 5 μL.

In a case where the normal analysis flow passage has the first mixer, even when a mobile phase passes through the first mixer having a capacity that is small for a mobile phase flow rate used in normal analysis, problems will not arise in sending of the mobile phase. This is because, in the case of normal analysis, the first mixer does not play a role in promoting the mixing of solvents, and therefore the position of the first mixer does not affect analysis. On the other hand, in the case of concentration analysis, when a mobile phase sent at a micro flow rate passes through the second mixer, the flow rate of the mobile phase is too small for the capacity of the second mixer and therefore a long delay occurs in sending of the mobile phase. For this reason, the concentration analysis flow passage does not have the second mixer.

In the liquid chromatograph according to the present invention, flow passage switching is carried out so that, in the case of normal analysis, a normal analysis flow passage is formed by connecting the mobile-phase-sending-unit, the second mixer, the sample injection portion, the analysis column and the detector in this order, and in the case of sample concentration, a concentration flow passage is formed by connecting the concentration liquid sending unit, the sample injection portion and the trapping column, and in the case of concentration analysis, a concentration analysis flow passage is formed by connecting the mobile-phase-sending-unit, the first mixer, the trapping column, the analysis column and the detector in this order, and further the flow rate of a mobile phase is made smaller in concentration analysis than in normal analysis. Therefore, in both cases of normal analysis using a mobile phase sent at a relatively large flow rate and concentration analysis using a mobile phase sent at a relatively small flow rate, it is possible to promote the mixing of solvents using a mixer having a capacity suitable for the flow rate of a mobile phase. This makes it possible to sufficiently mix solvents irrespective of the flow rate of a mobile phase and therefore to improve analytical reproducibility without causing a delay in sending of the mobile phase.

DETAILED DESCRIPTION OF THE INVENTION

Figure 1:
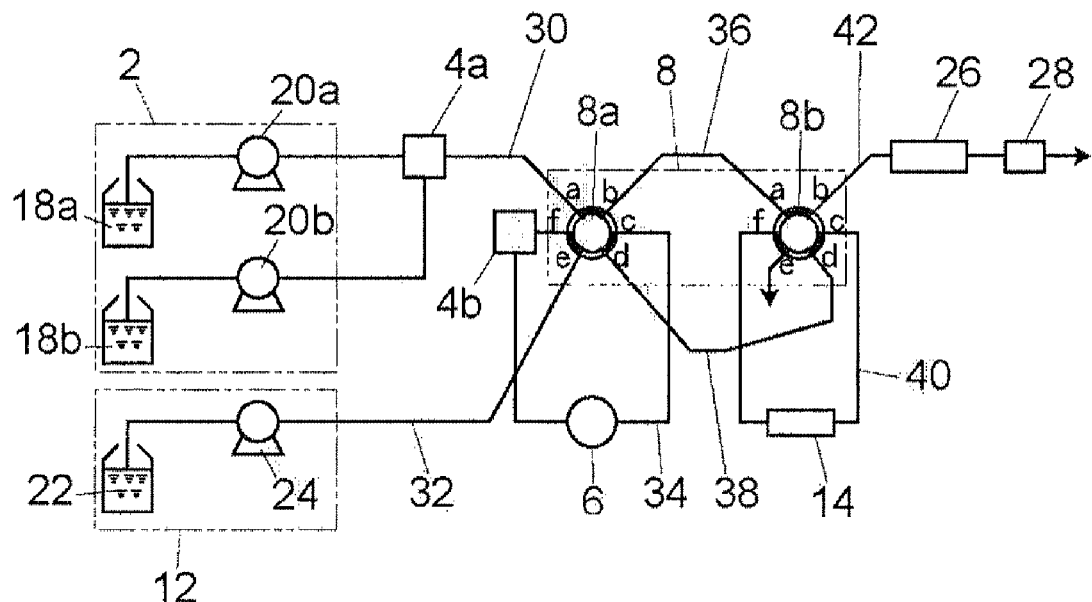
FIG. 1 is a diagram showing the flow passage configuration of a liquid chromatograph according to one embodiment of the present invention.

Hereinafter, a liquid chromatograph according to one embodiment of the present invention will be described. FIG. 1 is a diagram specifically showing the flow passage configuration of the liquid chromatograph according to one embodiment of the present invention.

A flow passage switching mechanism 8 has two first and second flow passage switching valves 8a and 8b as multi-port valves. The flow passage switching valves 8a and 8b are two-position six-port valves each having six ports numbered a to f clockwise. Each of the flow passage switching valves 8a and 8b is set to allow the ports a and b adjacent to each other to be connected to each other, the ports c and d adjacent to each other to be connected to each other, and the ports e and f adjacent to each other to be connected to each other at the same time and to allow, at another timing, the ports a and f adjacent to each other to be connected to each other, the ports b and c adjacent to each other to be connected to each other, and the ports d and e adjacent to each other to be connected to each other at the same time.

To the port a of the flow passage switching valve 8a, a mobile phase flow passage 30 is connected. The mobile phase flow passage 30 is connected downstream of a micro mixer 4. The micro mixer 4 is provided as a first mixer at a junction of two flow passages for sending two kinds of solvents contained in containers 18a and 18b by the use of liquid sending pumps 20a and 20b. The micro mixer 4 has a capacity of, for example, 5 μL. The containers 18a and 18b and the liquid sending pumps 20a and 20b constitute a mobile-phase-sending-unit 2.

The port b of the flow passage switching valve 8a and the port a of the flow passage switching valve 8b are connected to each other via a port-to-port connection flow passage 36. Further, the port d of the flow passage switching valve 8a and the port d of the flow passage switching valve 8b are connected to each other via a port-to-port connection flow passage 38.

A sample injection portion 6 is provided in a sample injection flow passage 34. One end of the sample injection flow passage 34 is connected to the port c of the flow passage switching valve 8a and the other end of the sample injection flow passage 34 is connected to the port f of the flow passage switching valve 8a. In this flow passage configuration, the end of the sample injection flow passage 34 connected to the port f of the flow passage switching valve 8a is an upstream end, and the end of the sample injection flow passage 34 connected to the port c of the flow passage switching valve 8a is a downstream end. In the sample injection flow passage 34, a conventional mixer 4b as a second mixer is provided upstream of the sample injection portion 6. The conventional mixer 4b has a capacity of, for example, 1 mL.

It is to be noted that in the liquid chromatograph, the micro mixer 4a is provided at a junction of two flow passages constituting the mobile-phase-sending-unit 2 so that a mobile phase sent from the mobile-phase-sending-unit 2 passes through the micro mixer 4 irrespective of the flow rate of the mobile phase. This is because in a case where the flow rate of a mobile phase sent from the mobile-phase-sending-unit 2 is large, the capacity of the micro mixer 4 does not have a great influence on the sending of the mobile phase.

To the port e of the flow passage switching valve 8a, a liquid flow passage 32 is connected. The liquid flow passage 32 is provided for sending a liquid stored in a container 22 by the use of a liquid sending pump 24. The liquid stored in the container 22 is used for transferring a sample to be concentrated. The container 22 and the liquid sending pump 24 constitute a concentration liquid sending unit 12 for sending a liquid for transferring a sample to be concentrated.

To the port b of the flow passage switching valve 8b, an analysis flow passage 42 is connected. In the analysis flow passage 42, an analysis column 26 and a detector 28 are provided. A trapping column 14 is provided in a trapping column flow passage 40. One end of the trapping column flow passage 40 is connected to the port c of the flow passage switching valve 8b, and the other end of the trapping column flow passage 40 is connected to the port f of the flow passage switching valve 8b. The port e of the flow passage switching valve 8b is connected to a drain.

In the liquid chromatograph according to the present embodiment, the flow passage switching valve 8a is used to switch between normal analysis and concentration analysis, and the flow passage switching valve 8b is used to switch between a sample concentration step and an analysis step during concentration analysis. Hereinafter, an analytical method using the liquid chromatograph according to the present embodiment will be described.

<Normal Analysis>

Figure 2:
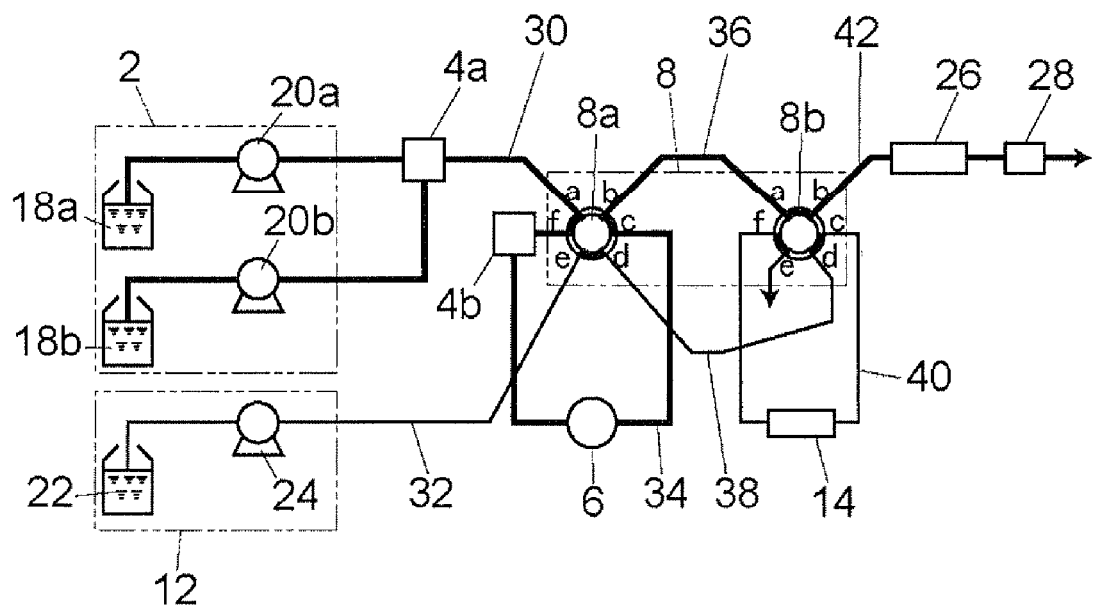
FIG. 2 is a diagram showing the flow passage configuration of the liquid chromatograph according to the present embodiment during normal analysis.

FIG. 2 is a diagram showing the flow passage configuration of the liquid chromatograph during normal analysis not using a trapping column. In FIG. 2, a thick line denotes a flow passage through which a mobile phase flows. The flow passage switching valve 8a is operated so that the ports a and f are connected to each other, the ports b and c are connected to each other, and the ports d and e are connected to each other, and the flow passage switching valve 8b is operated so that the ports a and b are connected to each other, the ports c and d are connected to each other, and the ports e and f are connected to each other. As a result, the sample injection flow passage 34 is connected downstream of the mobile phase flow passage 30, the port-to-port connection flow passage 36 is connected to the sample injection flow passage 34, and the analysis flow passage 42 is connected to the port-to-port connection flow passage 36 so that a normal analysis flow passage is formed.

A mobile phase containing two kinds of solvents is sent from the mobile-phase-sending-unit 2 at a conventional flow rate larger than 50 μL/min. The mobile phase sent from the mobile-phase-sending-unit 2 passes through both of the micro mixer 4a and the conventional mixer 4b, but the mobile phase is sufficiently mixed particularly by the conventional mixer 4b and then passes through the sample irjection flow passage 34 to transfer a sample injected from the sample injection portion 6 to an analysis unit 10. The sample transferred to the analysis unit 10 by the mobile phase is separated into individual components by the analysis column 26. The individual components separated by the analysis column 26 are further transferred to and detected by the detector 28.

In the case of normal analysis, since the mobile phase sent from the mobile-phase-sending-unit 2 passes through the conventional mixer 4b having a large capacity suitable for mixing a solvent sent at a conventional flow rate, the mobile phase can be sufficiently mixed.

<Concentration Analysis>

Figure 3A:
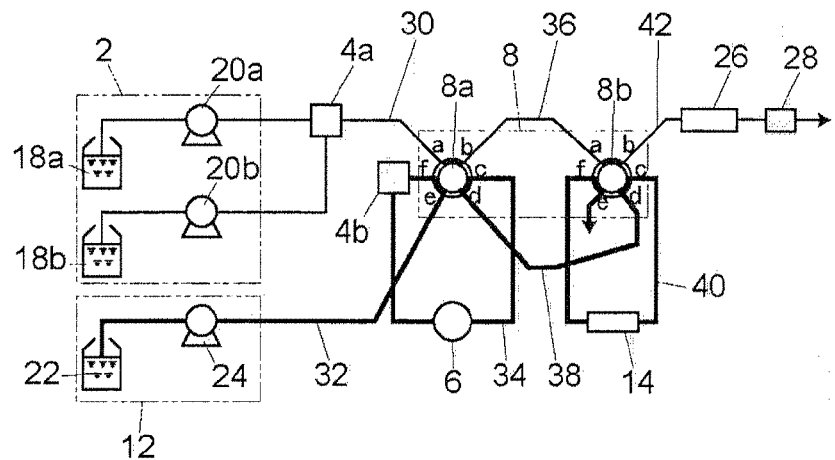
FIG. 3A is a diagram showing the flow passage configuration of the liquid chromatograph according to the present embodiment during sample concentration.
Figure 3B:
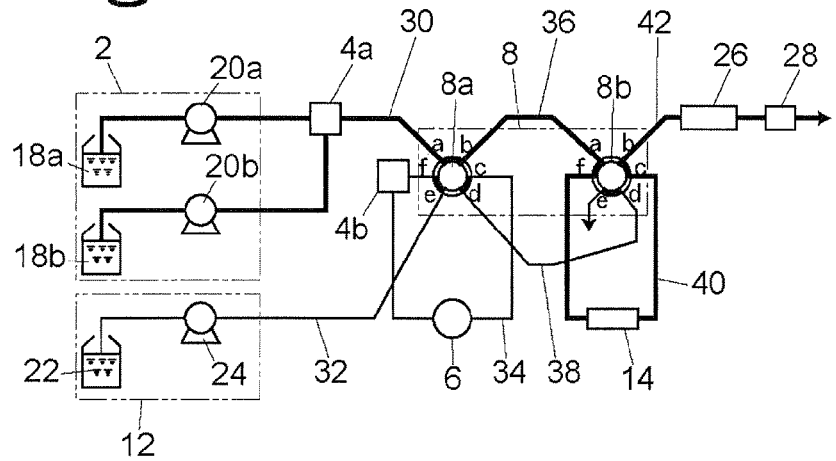
FIG. 3B is a diagram showing the flow passage configuration of the liquid chromatograph according to the present embodiment during concentration analysis.

The flow passage configuration of the liquid chromatograph in a case of concentration analysis when a sample is concentrated using a trapping column, and then an analysis is conducted using the concentrated sample is shown in FIG. 3A and FIG. 3B.

FIG. 3A is a diagram showing the flow passage configuration of the liquid chromatograph in a step of concentrating a sample using a trapping column during concentration analysis, wherein a thick line denotes a flow passage through which a liquid for transferring a sample to be concentrated flows. FIG. 3B is a diagram showing the flow passage configuration of the liquid chromatograph in a step of analyzing a concentrated sample during concentration analysis, wherein a thick line denotes a flow passage through which a mobile phase flows.

In the case of concentration analysis, the flow passage switching valve 8a is operated so that the ports a and b are connected to each other, the ports c and d are connected to each other, and the ports e and f are connected to each other in both of the sample concentration step and the concentration analysis step.

(Sample Concentration Step)

In the sample concentration step, as shown in FIG. 3A, the flow passage switching valve 8b is operated so that the ports a and b are connected to each other, the ports c and d are connected to each other, and the ports e and f are connected to each other. As a result, the sample injection flow passage 34 is connected downstream of the liquid flow passage 32, the port-to-port connection flow passage 38 is connected to the sample injection flow passage 34, and the trapping column flow passage 40 is connected to the port-to-port connection flow passage 38 so that a concentration flow passage is formed.

A liquid for transferring a sample to be concentrated is sent from the concentration liquid sending unit 12 at a flow rate of, for example, 100 μL/min. The liquid for transferring a sample to be concentrated passes through the sample injection flow passage 34, and then reaches the trapping column 14 together with a sample injected from the sample injection portion 6. As a result, the sample is concentrated because only the sample is trapped in the trapping column 14. The liquid for transferring a sample to be concentrated introduced into the trapping column 14 together with the sample passes through the trapping column 14 without being trapped, and is then discharged into a drain. It is to be noted that the liquid for transferring a sample to be concentrated is a single-component liquid, and therefore it is not necessary to allow the liquid to pass through the mixer, but the liquid for transferring a sample to be concentrated passes through the conventional mixer 4b because of the flow passage configuration of the liquid chromatography. However, this causes no problem because a long delay does not occur in sending the liquid for transferring a sample to be concentrated, judging from the flow rate of the liquid sent from the concentration liquid sending unit 12.

(Concentration Analysis Step)

Next, as shown in FIG. 3B, the flow passage switching valve 8b is operated so that the ports a and f are connected to each other, the ports c and d are connected to each other, and the ports e and f are connected to each other. As a result, the port-to-port connection flow passage 36 is connected downstream of the mobile phase flow passage 30, the trapping column flow passage 40 is connected to the port-to-port connection flow passage 36, and the analysis flow passage 42 is connected to the trapping column flow passage 40 so that a concentration analysis flow passage is formed.

A mobile phase containing two kinds of solvents is sent from the mobile-phase-sending-unit 2 at a micro flow rate of, for example, 5 μL/min. The mobile phase is sufficiently mixed by the micro mixer 4a, and then reaches the analysis unit 10 through the port-to-port connection flow passage 36 and the trapping column flow passage 40. The sample trapped in the trapping column 14 is eluted with the mobile phase passes through the trapping column 14, and then the sample is introduced into the analysis unit 10 together with the mobile phase. The sample introduced into the analysis unit 10 is separated into individual components by the analysis column 26, and the individual components are transferred to and detected by the detector 28.

In the concentration analysis step, since the mobile phase sent at a micro flow rate does not pass through the conventional mixer provided as the second mixer having a capacity too large for the micro flow rate but passes through only the micro mixer 4a, a delay resulting from the capacity of the mixer does not occur in sending the mobile phase.

In the liquid chromatograph according to the present embodiment described with reference to FIGS. 1, 2, 3A and 3b, in the case of normal analysis, a mobile phase sent at a conventional flow rate passes through both of the micro mixer (first mixer) 4a and the conventional mixer (second mixer) 4b, and the mixing of the mobile phase is promoted by the conventional mixer 4b, On the other hand, in the case of concentration analysis, a mobile phase sent at a micro flow rate passes through the micro mixer 4a to promote the mixing of the mobile phase. In this case, the mobile phase is not allowed to pass through the conventional mixer 4b to prevent the occurrence of a delay in sending the mobile phase.

Figure 4:
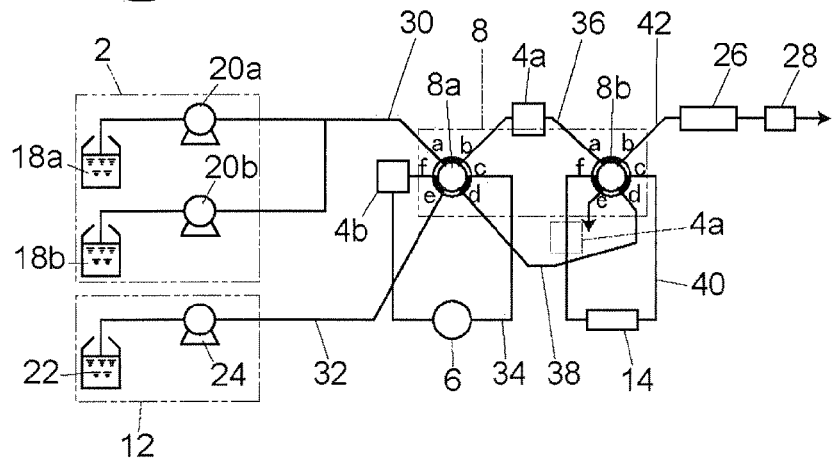
FIG. 4 is a diagram showing the flow passage configuration of a liquid chromatograph according to another embodiment of the present invention.

Further, in the liquid chromatograph according to the present embodiment described with reference to FIGS. 1, 2, 3A and 3B, the micro mixer 4a is provided at a junction of two flow passages constituting the mobile-phase-sending-unit 2. However, as shown in FIG. 4, the micro mixer 4a may be provided on the port-to-port connection flow passage 36. Alternatively, the micro mixer 4a may be provided at a position denoted by a broken line in FIG. 4 so as to be connected to the port f of the flow passage switching valve 8b connected to the trapping column 14. Also in the case of a liquid chromatograph having a structure shown in FIG. 4, a flow passage can be switched among a normal analysis flow passage, a concentration flow passage, and a concentration analysis flow passage by operating the flow passage switching valves 8a and 8b in the same manner as in the case of the liquid chromatograph according to the present embodiment described above.

What is claimed is:

1. A liquid chromatograph comprising:
   a mobile-phase-sending-unit having a plurality of solvent flow passages for sending solvents different from each other;
   a mixer unit provided downstream of the mobile-phase-sending-unit to mix solvents sent from the mobile-phase-sending-unit, the mixer unit having a first mixer and a second mixer having a capacity larger than that of the first mixer;
   a sample injection portion for injecting a sample;
   a concentration liquid sending unit for sending a liquid for transferring a sample to be concentrated;
   a trapping column for concentrating the sample by trapping components of the sample;
   an analysis column for separating the sample into individual components;
   a detector for detecting each of the components separated by the analysis column; and
   a flow passage switching mechanism having a first multi-port valve connected to the second mixer and the sample injection portion, a second multi-port valve connected to the trapping column and the analysis column, and a port-to-port connection flow passage for connecting the first and second multi-port valves, wherein the first mixer is connected to the first multi-port valve, the second multi-port valve or the port-to-port connection flow passage,
   the flow passage switching mechanism switching among a normal analysis flow passage formed by connecting the mobile-phase-sending-unit, the second mixer, the sample injection portion, the analysis column and the detector in this order, a concentration flow passage formed by connecting the concentration liquid sending unit, the second mixer, the sample injection portion and the trapping column in this order, and a concentration analysis flow passage formed by connecting the mobile-phase-sending-unit, the first mixer, the trapping column, the analysis column, and the detector in this order so that any one of the three flow passages is selectively formed, and
   the mobile-phase-sending-unit being set so that the flow rate of a mobile phase becomes smaller when the concentration analysis flow passage is selected than when the normal analysis flow passage is selected.

2. The liquid chromatograph according to claim 1,
   wherein the first mixer is connected to the first multi-port valve, and
   wherein the normal analysis flow passage is formed by connecting the mobile-phase-sending-unit, the first mixer, the second mixer, the sample injection portion, the analysis column and the detector in this order.

3. The liquid chromatograph according to claim 1,
   wherein the first mixer is connected to the port-to-port connection flow passage, and
   wherein the normal analysis flow passage is formed by connecting the mobile-phase-sending-unit, the second mixer, the sample injection portion, the first mixer, the analysis column and the detector in this order.

4. The liquid chromatograph according to claim 1,
   wherein the first mixer is connected to a port of the second multi-port valve, the port sending liquid to the trapping column, and
   wherein the normal analysis flow passage is formed by connecting the mobile-phase-sending-unit, the second mixer, the sample injection portion, the analysis column and the detector in this order.

* * * * *